US00PP36370P2

(12) United States Plant Patent
Serna

(10) Patent No.: US PP36,370 P2
(45) Date of Patent: Jan. 7, 2025

(54) MANDARIN PLANT NAMED 'CLEMENLOLA'

(50) Latin Name: *Citrus clementina hort.*
Varietal Denomination: Clemenlola

(71) Applicant: Clemenfort S.L., Alicante (ES)

(72) Inventor: Dolores Juan Serna, Alicante (ES)

(73) Assignee: CLEMENFORT S.L., Alicante (ES)

( * ) Notice: Subject to any disclaimer, the term of this patent is extended or adjusted under 35 U.S.C. 154(b) by 0 days.

(21) Appl. No.: 18/511,136

(22) Filed: Nov. 16, 2023

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201
CPC ..... A01H 6/785; A01H 5/08
See application file for complete search history.

(56) References Cited

PUBLICATIONS

Clemenlola with English Translation uploaded to CVVP webpage Feb. 23, 2023. (2 pages) URL: https://www.clubvvp.com/wp-content/uploads/2023/02/230213_folleto_CLEMENLOLA_OK.pdf.
Clemenlola, mayor precocidad y calibre by CítricosCVVP webpage Mar. 27, 2023 (2 pages) URL: https://revistamercados.com/clemenlola-mayor-precocidad-y-calibre/.
Variety description of CPVO on Mar. 2023. (16 pages).
Certificado Relativo a la Concesión de la Protección Comunitaria de las Obtenciones Vegetales on Mar. 2023. (2 pages).

*Primary Examiner* — Keith O. Robinson
(74) *Attorney, Agent, or Firm* — WHDA, LLP

(57) ABSTRACT

'CLEMENLOLA' is a spontaneous mutation of the variety 'Oronules' originating in Albatera (Alicante). It is a variety that is easy to peel, with a firm skin and flattened shape, with a high juice content. The tree is vigorous, open growing and has no thorns or multi-branches. It is also an early and productive variety, reaching maturity in the last week of September and during the month of October.

8 Drawing Sheets

Latin name of the genus and species of the plant claimed: *Citrus clementina hort.* ex Tanaka.

Variety denomination: Mandarin plant 'CLEMENLOLA'.

BACKGROUND OF THE INVENTION

The new and distinct mandarin cultivar of the present invention was discovered while growing in a town of the Alicante region of Spain called Albatera while present among standard 'Oronules' mandarin trees non-patented. A single plant of the new cultivar was found in 2016, was carefully preserved and subsequently asexually reproduced in order to confirm that the variety is distinct, uniform and stable.

The new invention called 'CLEMENLOLA' is precocious and productive. The color is reddish orange and is absent or contains very few seeds in the main harvest. It is easy to peel with firmer skin, flatter shape and it has high juice content. The tree is vigorous with open growth, and it does not have thorns or multi-buds.

The 'Oronules' variety is grown in Albatera (Alicante), so the comparative studies have been carried out under homogeneous growing and climatic conditions, and the characteristics described have been found to be attributable to the genotype.

Had the new cultivar of the present invention not been discovered and preserved, it would have been lost to mankind. This new cultivar is believed to be a spontaneous mutation of the 'Oronules' mandarin tree of unknown causation.

It was found that the new mandarin cultivar of the present invention forms attractive fruit which when compared to the 'Oronules' (not-patented) cultivars displays an earlier season of maturity.

The new cultivar has been asexually reproduced in the Alicante region of Spain by grafting on *Citrus macrophylla* rootstock (not-patented). There are no special breeding conditions. These are those for citrus fruits with virus-free rods. Accordingly, the new cultivar reproduces in a true-to-type manner by such asexual reproduction.

The new cultivar can be readily distinguished from 'Oronules' because it has a low anther (viable pollen), the fruit length is shorter and the fruit diameter is small, the fruit number of seeds is very few or few instead of many numbers of seeds that the 'Oronules' variety has. Both varieties have a different evolution in the ripening curves in terms of percentage of sugars, acidity and ripeness index observed in the final development phase of the fruit.

SUMMARY OF THE INVENTION

Noticeable characteristics of the inventive variety 'CLEMENLOLA' are as follows:

(1) 'CLEMENLOLA' has fewer seeds than the 'Oronules' Mandarin variety has.
(2) 'CLEMENLOLA' has low anther (viable pollen).
(3) 'CLEMENLOLA' has shorter length size and flatter fruit shape than the 'Oronules' Mandarin variety.
(4) 'CLEMENLOLA' has a different evolution in the ripening curves in terms of the percentage of sugars, acidity and ripeness index observed in the final development phase of the fruit.

(5) 'CLEMENLOLA' produces fruits with virus-free rods.

DETAILED DESCRIPTION OF THE INVENTION

Figure 1:
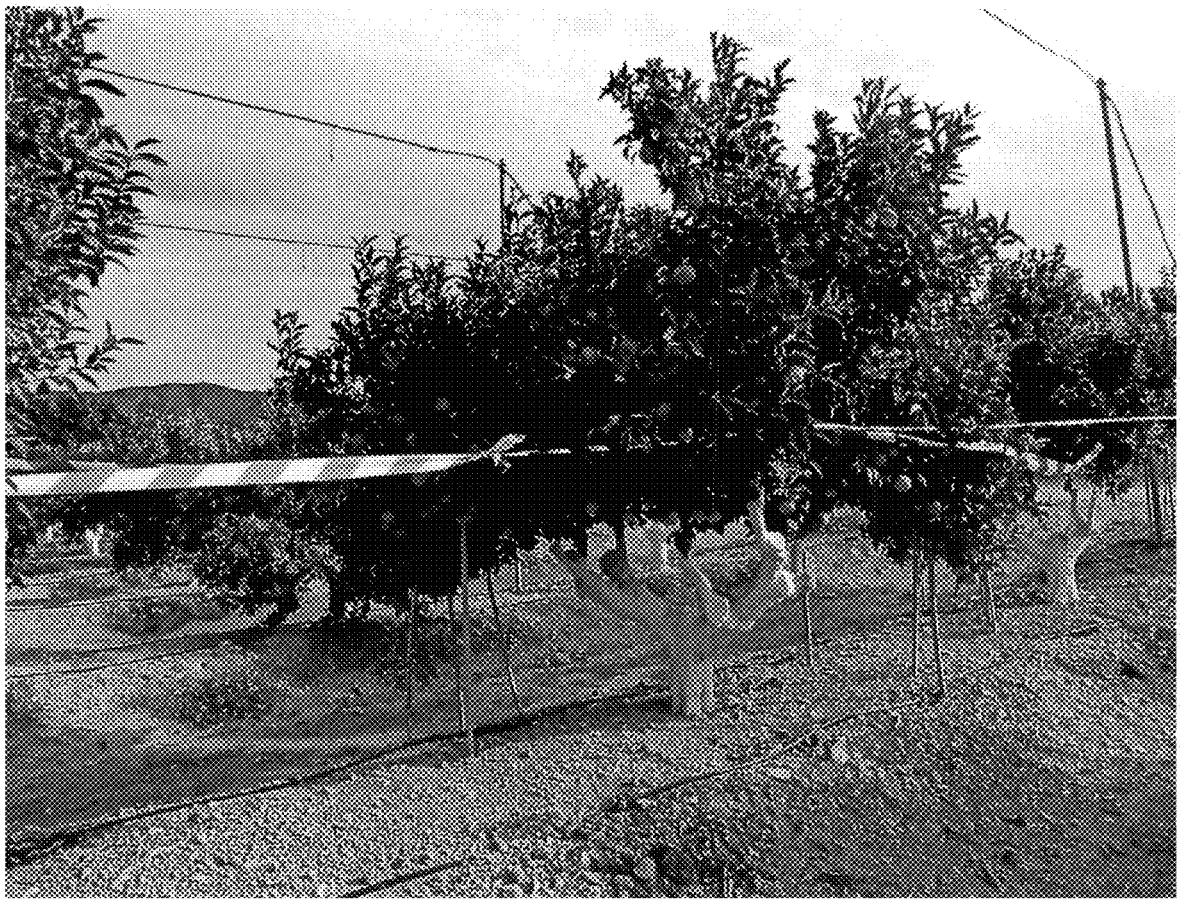
FIG. 1 is a photograph showing a tree of 'CLEMENLOLA' that the age of the tree is 26 years but the tree was grafted on 2006 with the CLEMENLOLA variety.
Figure 2:
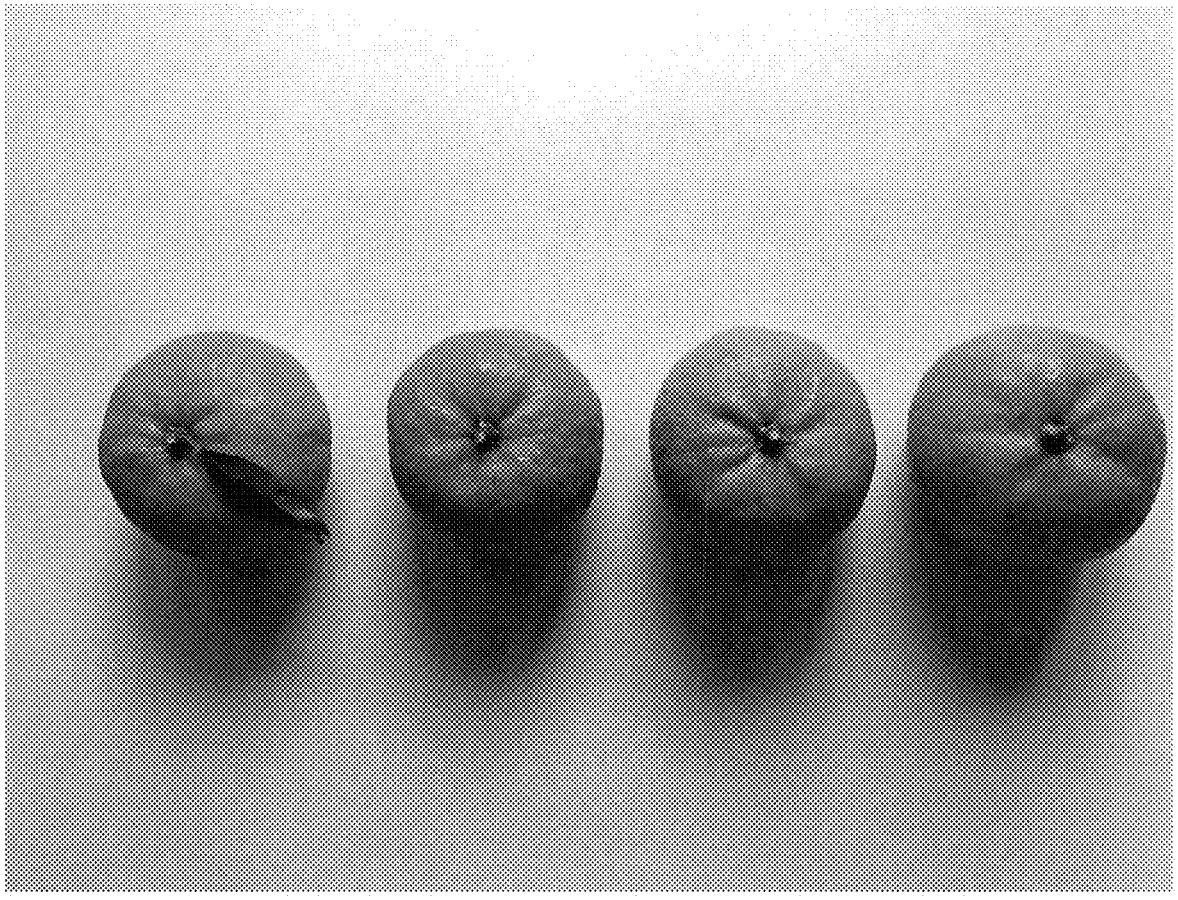
FIG. 2 is a photograph showing a top view of a fruit body of 'CLEMENLOLA'.
Figure 3:
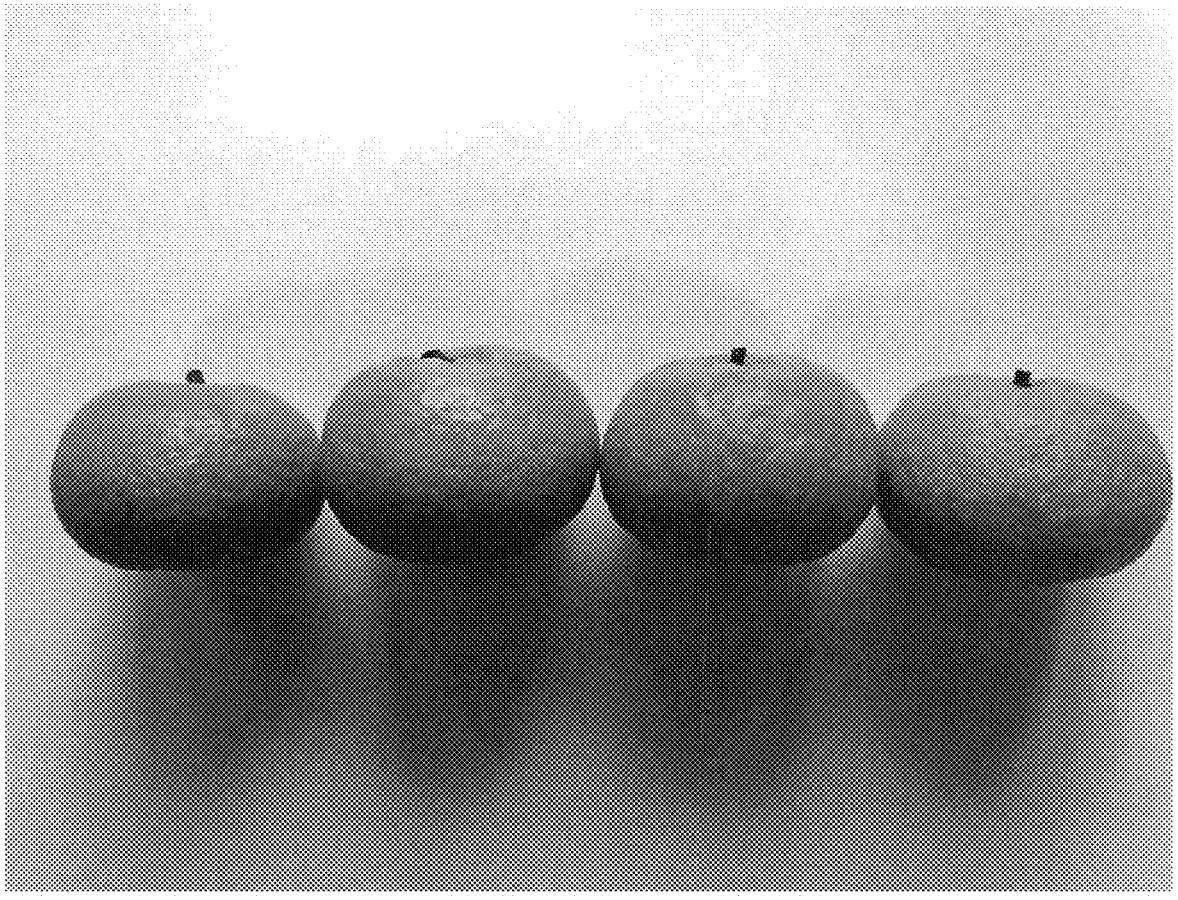
FIG. 3 is a photograph showing a side view of a fruit body of 'CLEMENLOLA'.
Figure 4:
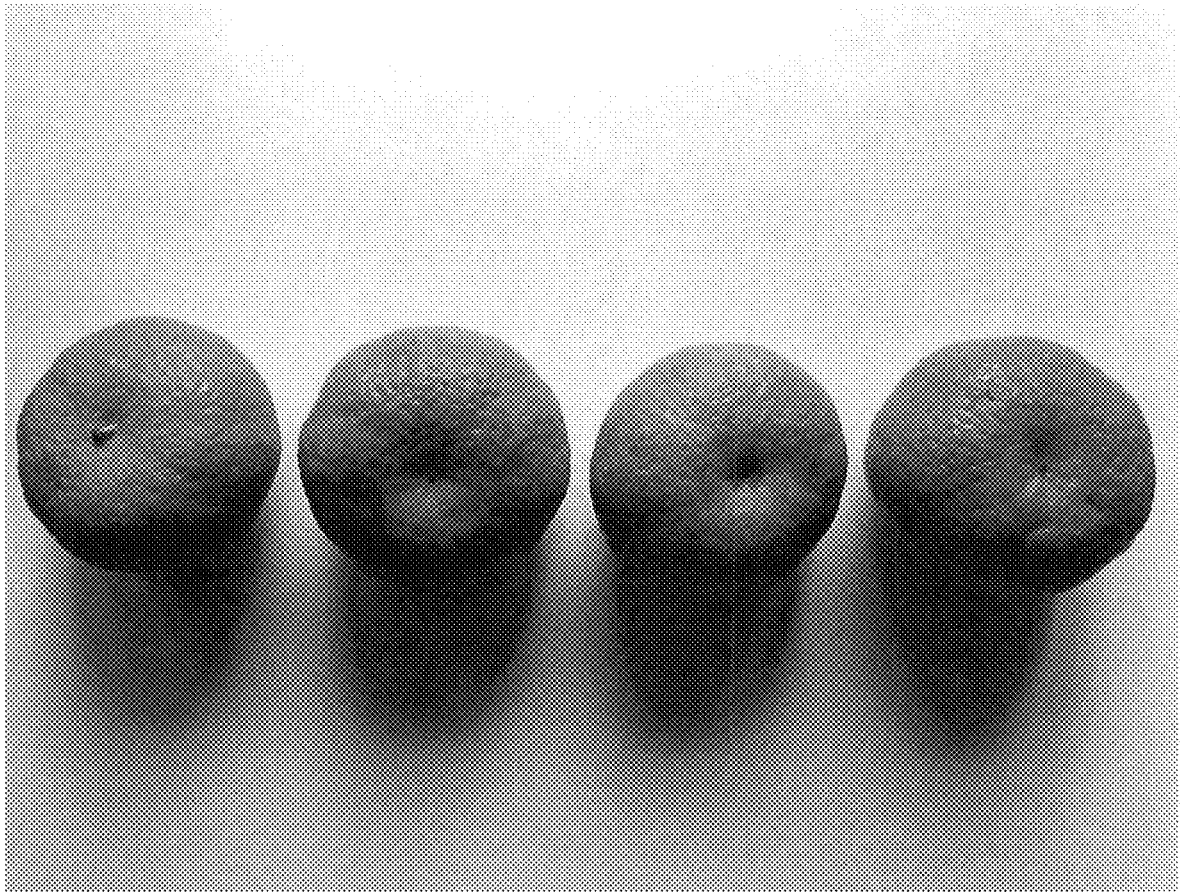
FIG. 4 is a photograph showing a bottom view of a fruit body of 'CLEMENLOLA'.
Figure 5:
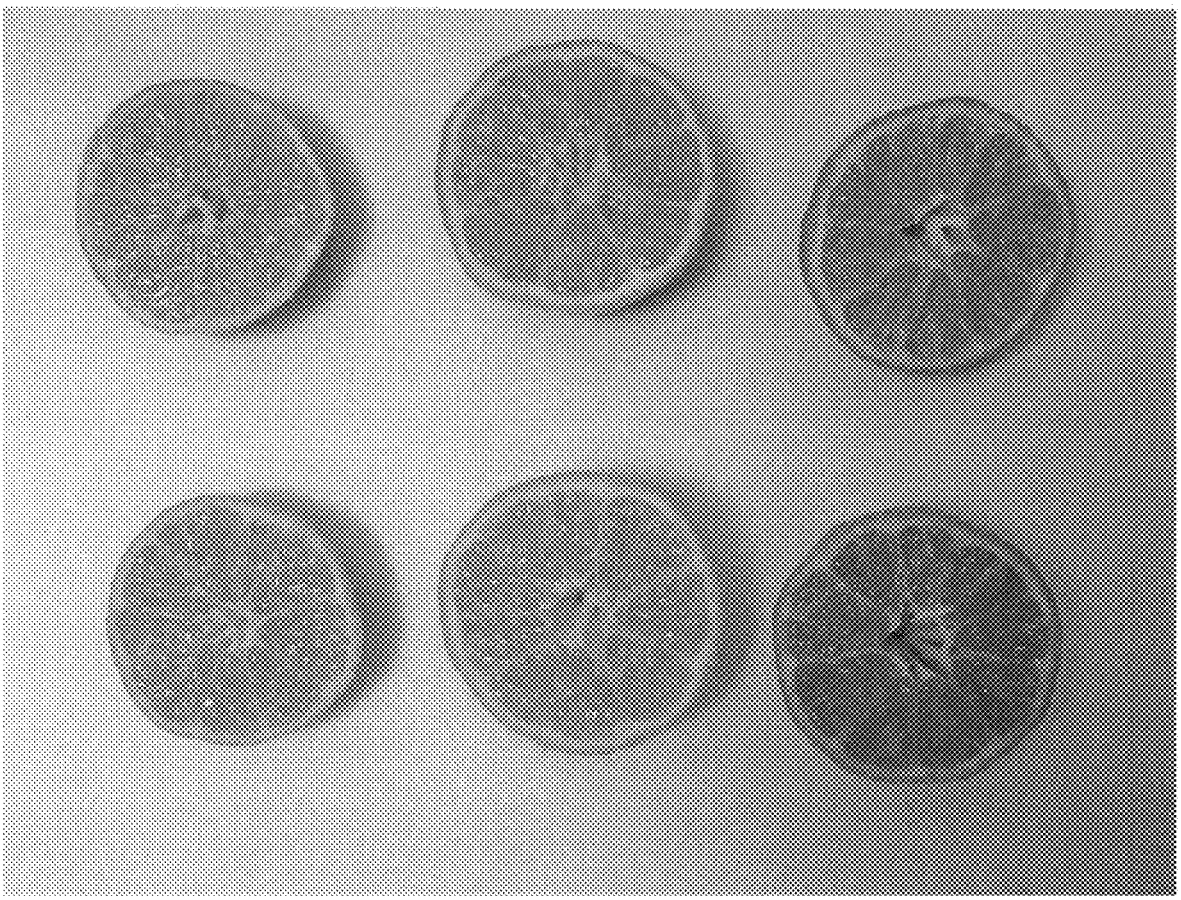
FIG. 5 is a photograph showing a sectional view of a fruit body of 'CLEMENLOLA'.
Figure 6:
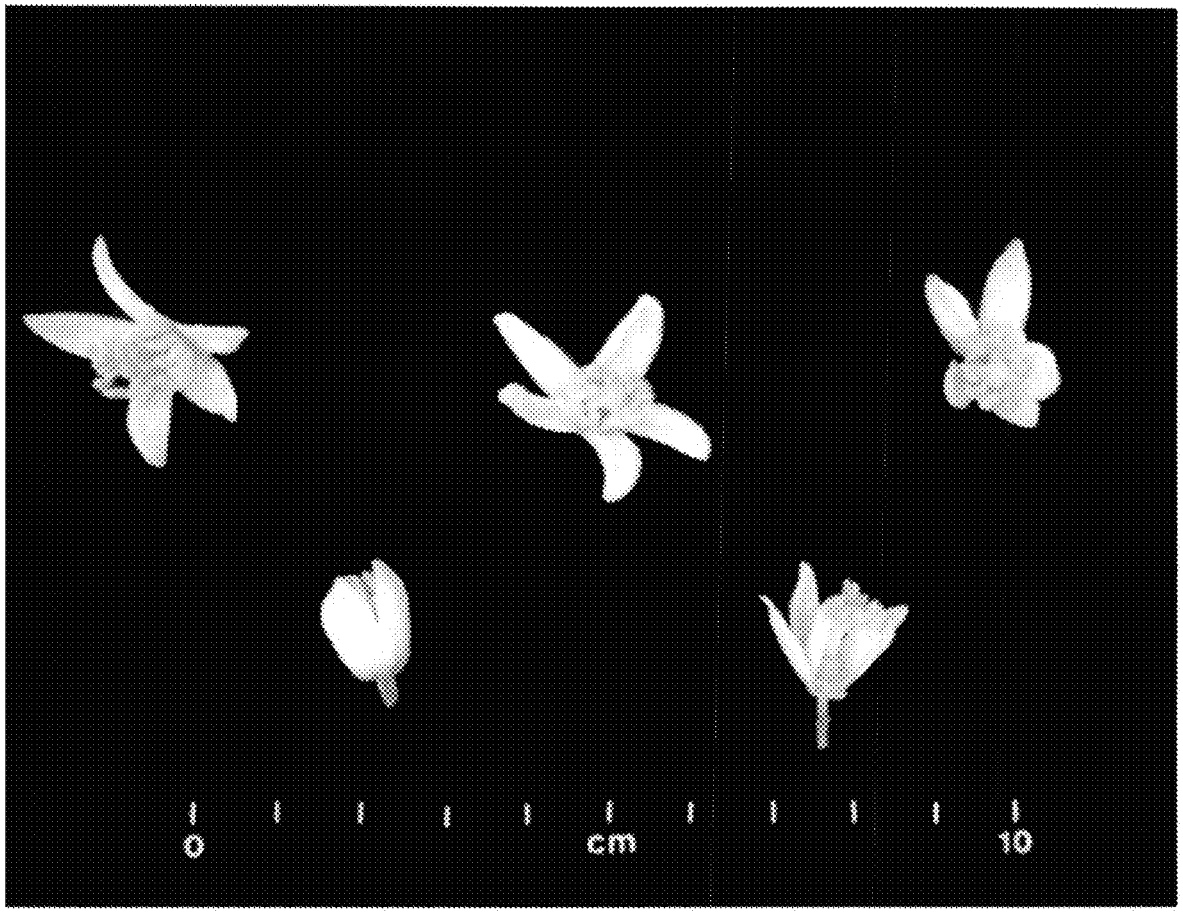
FIG. 6 is a photograph showing different views of a flower of 'CLEMENLOLA'.
Figure 7:
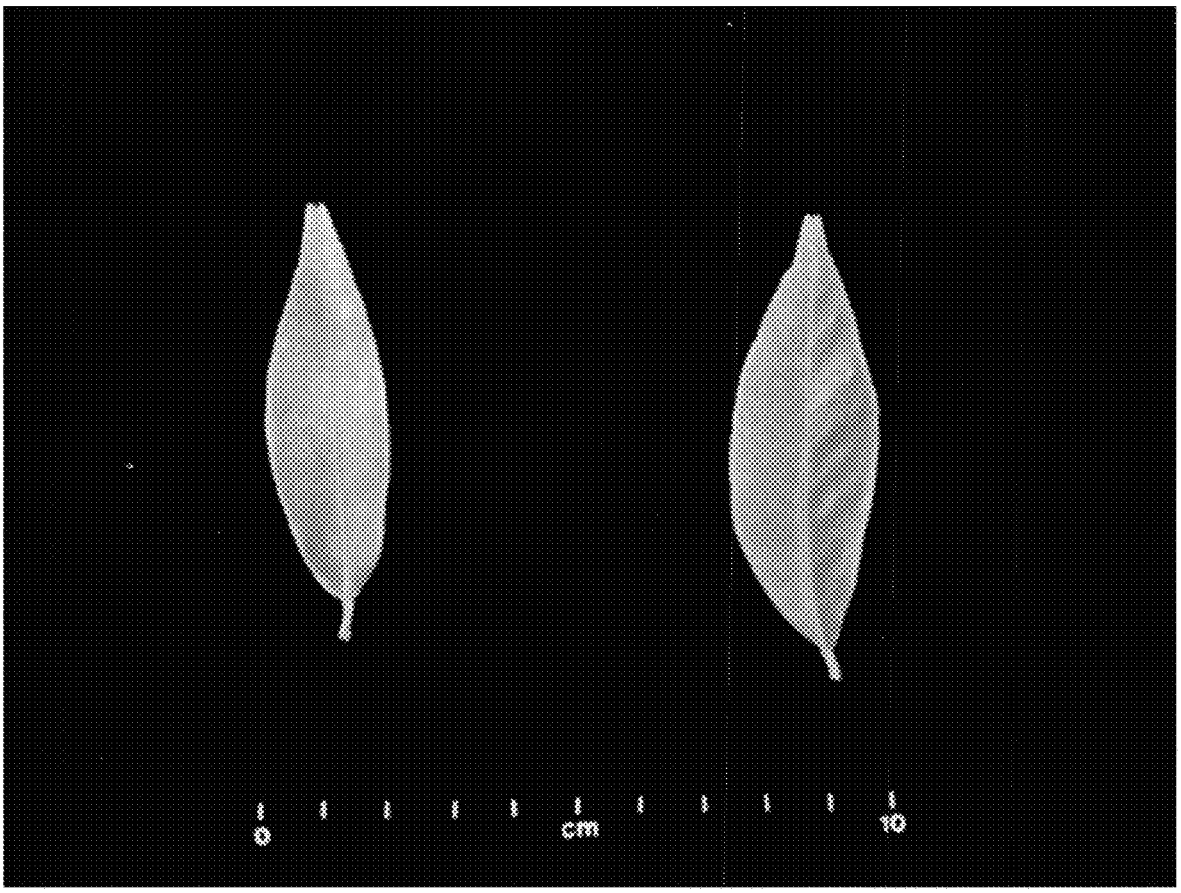
FIG. 7 is a photograph showing a front view of a leaf of 'CLEMENLOLA'.
Figure 8:
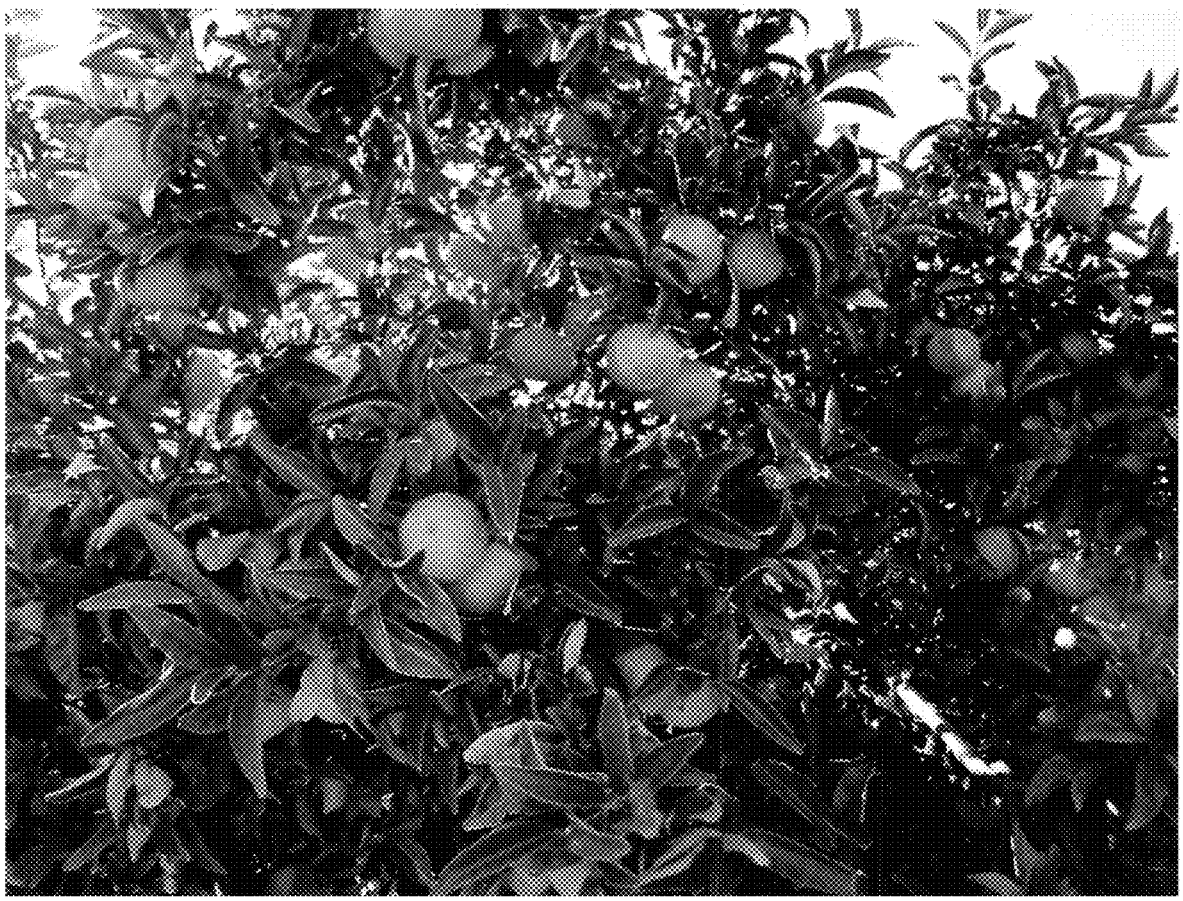
FIG. 8 is a photograph showing the cultivation of 'CLEMENLOLA'.

The described plants of the new cultivar had been asexually reproduced by grafting on *Citrus clementina hort*. ex Tanaka outdoors in full sunlight in the Alicante region of Spain. Observations obtained during the growing season of 2022 are presented.

Classification: *Citrus clementina hort*. ex Tanaka.

Breeding scheme: Spontaneous mutation of the 'Oronules' Mandarin tree.

Method of propagation of the variety: vegetatively propagated by grafting.

Characteristics of the variety:

*Young leaf*.—Presence of anthocyanin coloration: Absent.

*Young leaf*.—Intensity of anthocyanin coloration: None.

*Fruit length*.—42~45 mm (short to medium).

*Fruit diameter*.—55~65 mm (medium).

*Fruit shape*.—Flattened. Fruit — presence of neck: Absent. Fruit — presence of nipple: Absent. Fruit — presence of areola: Incomplete. Fruit surface — predominant color: Orange red, Group 30 A obtained from [RHS Colour Chart—Sixth Edition 2015]. Fruit — main color of flesh: Medium orange, Group 28 B obtained from [RHS Colour Chart—Sixth Edition 2015]. The adherence to the fresh of the fruit rind: Weak. Fruit — the amount of albedo adhering to the fresh of the fruit: Small.

*The presence of the navel of the fruit*.—absent or very rare.

*Parthenocarpy*.—Present.

*Juiciness*.—Medium/High.

*The total soluble solid of the fruit juice*.—Medium.

*The growth habit of the claimed plant*.—Spreading.

*The position of the broadest part of the fruit*.—At middle.

*The presence of depression at the stalk end*.—Absent.

*The thickness of the fruit rind*.—Medium to Thick.

*The oiliness of the fruit rind*.—Oily.

*The glossiness of the fruit surface*.—Medium.

*The polyembryony of the seed*.—Present.

*The flowering habit of the plant*.—Flowering once.

*The time of maturity of fruit for consumption*.—Early.

What is claimed is:

1. A new and distinct variety of mandarin plant named 'CLEMENLOLA' substantially as illustrated and described herein.

* * * * *